(12) United States Patent
Suchy

(10) Patent No.: US 11,869,154 B2
(45) Date of Patent: Jan. 9, 2024

(54) METHOD AND SYSTEM FOR VISUALISING A SPATIAL SURFACE CURVATURE OF A 3D-OBJECT, COMPUTER PROGRAM PRODUCT, AND COMPUTER-READABLE STORAGE MEDIUM

(71) Applicant: Siemens Healthcare GmbH, Erlangen (DE)

(72) Inventor: Bjoern Suchy, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 1073 days.

(21) Appl. No.: 16/590,492

(22) Filed: Oct. 2, 2019

(65) Prior Publication Data

US 2020/0107888 A1 Apr. 9, 2020

(30) Foreign Application Priority Data

Oct. 9, 2018 (EP) .................................... 18199333

(51) Int. Cl.
*G06T 19/00* (2011.01)
*A61B 34/10* (2016.01)
(Continued)

(52) U.S. Cl.
CPC .......... *G06T 19/006* (2013.01); *A61B 34/10* (2016.02); *A61B 34/25* (2016.02); *A61B 90/361* (2016.02);
(Continued)

(58) Field of Classification Search
CPC ...... A61B 2090/365; A61B 2034/2065; A61B 34/10; A61B 2034/105; A61B 2090/367; A61B 34/25; G06T 19/006; G06T 7/75
See application file for complete search history.

(56) References Cited

U.S. PATENT DOCUMENTS

2004/0210125 A1* 10/2004 Chen ...................... A61B 34/20
600/407
2013/0328870 A1 12/2013 Grenfell
(Continued)

FOREIGN PATENT DOCUMENTS

| CN | 105378801 A | 3/2016 |
| CN | 107645656 A | 1/2018 |
| WO | WO 2018148845 A1 | 8/2018 |

OTHER PUBLICATIONS

European Office Action dated Feb. 4, 2021.
(Continued)

*Primary Examiner* — Joel Lamprecht
*Assistant Examiner* — Nyrobi Celestine
(74) *Attorney, Agent, or Firm* — Harness, Dickey & Pierce, P.L.C.

(57) ABSTRACT

A method and system are for acquiring a dataset created via an imaging modality, the dataset describing a 3D-shape of a 3D-object; adapting, in dependence on the 3D-shape of the 3D-object, a flat 2D-grid of intersecting grid lines to follow a surface curvature of the 3D-object to create an adapted grid, a distance between two neighbouring intersections, along the grid lines of the adapted grid following the surface curvature of the 3D-object, being equal to a respective corresponding distance between a respective two neighbouring intersections of the flat 2D-grid before the adapting; and outputting the adapted grid for display over at least one of the 3D-object and a virtual model of the 3D-object.

20 Claims, 3 Drawing Sheets

(51) Int. Cl.
   *A61B 34/00* (2016.01)
   *A61B 90/00* (2016.01)
   *G06T 7/73* (2017.01)
   *A61B 34/20* (2016.01)

(52) U.S. Cl.
   CPC .......... *G06T 7/75* (2017.01); *A61B 2034/105* (2016.02); *A61B 2034/2065* (2016.02); *A61B 2090/365* (2016.02); *A61B 2090/367* (2016.02)

(56) References Cited

U.S. PATENT DOCUMENTS

| | | | |
|---|---|---|---|
| 2014/0241511 | A1 | 8/2014 | Hausotte et al. |
| 2014/0306993 | A1 | 10/2014 | Poulos et al. |
| 2014/0343404 | A1* | 11/2014 | Razzaque ............ A61B 8/0841 600/424 |
| 2015/0257846 | A1* | 9/2015 | Kubiak ................. A61B 6/485 600/407 |
| 2018/0025530 | A1 | 1/2018 | Anthony et al. |
| 2018/0116726 | A1 | 5/2018 | Liang et al. |
| 2018/0168740 | A1 | 6/2018 | Ryan et al. |
| 2018/0168781 | A1* | 6/2018 | Kopelman ............ A61C 19/04 |
| 2019/0035156 | A1* | 1/2019 | Wei ........................ A61B 34/10 |
| 2019/0038362 | A1* | 2/2019 | Nash ..................... H04N 13/366 |
| 2019/0125459 | A1* | 5/2019 | Shelton, IV ........... G16H 40/63 |
| 2019/0183577 | A1* | 6/2019 | Fahim .................... G02B 27/01 |
| 2019/0206100 | A1* | 7/2019 | Batra ...................... G06T 11/60 |
| 2019/0311542 | A1* | 10/2019 | Douglas ................. A61B 6/547 |

OTHER PUBLICATIONS

Moeller H et al: "Synthetic Vision for Improving Flight Control in Night, Poor Visibility and Adverse Weather Conditions", Proceedings of the AIAA/IEEE Digital Avionics Systems Conference. New York, Oct. 25-28, 1993; [Proceedings of the AIAA/IEEE Digital Avionics Systems Conference], New York, IEEE, US, vol. Conf. 12; pp. 286-291; XP000451672.
Alethea S Bair et al: "Factors influencing the choice of projection textures for displaying layered surfaces", Applied Perception in Graphics and Visualization, ACM, 2 Penn Plaza, Suite 701 New York NY 10121-0701 USA; pp. 101-108, XP058297875, 001: 10.1145/1620993.1621014 ISBN: 978-1-60558-743-1.
Zigelman Gil * Kimmel R et al: "Texture mapping using surface flattening via multidimensional scaling", IEEE Transactions on Visualization and Computer Graphics, IEEE Service Center, Los Alamitos, CA, US, vol. 8, No. 2; pp. 198-207, XP011094455, ISSN: 1077-2626, 001: 10.1109/2945.998671.
Hui Fang et al: "RoloTexture: Automated Tools for Texturing Raw Video". IEEE Transactions ON Visualization and Computer Graphics, IEEE Service Center, Los Alamitos. CA, US, vol. 12, No. 6; pp. 1580-1589, XP011149149, ISSN: 1077-2626, 001: 10.1109/TVCG.2006.102.
European Office Action dated Feb. 27, 2020.
Wen Rong et al: "Hand gesture guided robot-assisted surgery based on a direct augmented reality interface"; Computer Methods and Programs in Biom Ed I Ci Ne , vol. 116, No. 2, Jan. 2, 2014 (Jan. 2, 20142), pp. 68-80, XP028872105; www.sciencedirect.com; ISSN: 0169-2607, DOI: 10.1016/J.CMPB.2013.12.018.
Extended European Search Report for European Application No. 18199333.8 dated Mar. 14, 2019.

* cited by examiner

METHOD AND SYSTEM FOR VISUALISING A SPATIAL SURFACE CURVATURE OF A 3D-OBJECT, COMPUTER PROGRAM PRODUCT, AND COMPUTER-READABLE STORAGE MEDIUM

PRIORITY STATEMENT

The present application hereby claims priority under 35 U.S.C. § 119 to European patent application number EP 18199333.8 filed Oct. 9, 2018, the entire contents of each of which are hereby incorporated herein by reference.

FIELD

Embodiments of the application generally relate to a method and a system for visualising a spatial surface curvature of a 3D-object, to a corresponding computer program product or computer program, and to a corresponding computer-readable storage medium.

BACKGROUND

Today, there is a vast array of different technical fields and applications that are concerned with understanding and manipulating 3D-objects, either in a real physical form, in a purely virtual form, or a mixture between the two. A correct understanding and awareness of spatial relations is essential for correct decisions and optimal results. One such technical field is the field of medical technology which is inherently concerned with the three-dimensional body where spatial relations between different body parts and tissues are essential for health and a correct functioning. In addition, there are many data-driven 3D-technologies established and being developed in the medical field. With the development and usage of these technologies there are inevitable challenges and opportunities for optimisation.

For example, in a typical scenario a surgeon receives radiological data and information about a patient. This radiological data can comprise volume data, positions, preliminary diagnostic findings, and the like. Often, such data is presented in the form of slice images, cut-away views, or volume renderings. The surgeon is then tasked with evaluating and interpreting the data to devise and plan an eventual future intervention.

SUMMARY

The inventors have recognized that a correct understanding and an optimal perceptibility of spatial relations, measures, and distances is an important factor for a successful intervention.

In view of the above, example embodiments for the embodiments described in the present application mainly focus on medical applications. It is to be understood, however, that the embodiments and claims of the present application are not limited to these examples or even to applications in the medical field but can be used or applied in a wide variety of different technical fields, industries, and applications.

Embodiments of the present invention facilitate an improved perceptibility of a spatial situation during interaction with a 3D-object. Advantageous embodiments with expedient developments of the present invention are indicated in the claims as well as in the description and in the drawings.

At least one embodiment of the present invention is directed to a method, comprising:

acquiring a dataset created via an imaging modality, the dataset describing a 3D-shape of a 3D-object;

adapting, in dependence on the 3D-shape of the 3D-object, a flat 2D-grid of intersecting grid lines to follow a surface curvature of the 3D-object to create an adapted grid, a distance between two neighbouring intersections, along the grid lines of the adapted grid following the surface curvature of the 3D-object, being equal to a respective corresponding distance between a respective two neighbouring intersections of the flat 2D-grid before the adapting; and outputting the adapted grid for display of the adapted grid over at least one of the 3D-object and a virtual model of the 3D-object.

Another aspect of an embodiment of the present invention is directed to a computer program product or computer program, comprising instructions that, when the computer program is executed by a computer, cause the computer to carry out a method according to an embodiment of the present invention for visualising a spatial surface curvature of a 3D-object.

The computer program product according to an embodiment of the present invention does, in other words, represent or encode the steps of the respective method or methods. The computer used for executing the computer program can in particular comprise a processor, a microchip, or a microcontroller, and a non-transitory computer-readable storage medium which is connected thereto and which contains the computer program or computer program product according to an embodiment of the present invention.

Such a non-transitory computer-readable storage medium having stored thereon a computer program product or computer program according to an embodiment of the present invention is in itself another embodiment of the present invention.

Correspondingly, another aspect of an embodiment of the present invention is directed to a data carrier signal carrying a computer program product or computer program according to an embodiment of the present invention.

Another aspect of an embodiment of the present invention is directed to a system comprising:

means for acquiring a dataset created via an imaging modality, the dataset describing a 3D-shape of a 3D-object;

means for adapting, in dependence on the 3D-shape of the 3D-object, a flat 2D-grid of intersecting grid lines to follow a surface curvature of the 3D-object to create an adapted grid, a distance between two neighbouring intersections, along the grid lines of the adapted grid following the surface curvature of the 3D-object, being equal to a respective corresponding distance between a respective two neighbouring intersections of the flat 2D-grid before the adapting; and means for outputting the adapted grid for display of the adapted grid over at least one of the 3D-object and a virtual model of the 3D-object.

Another aspect of an embodiment of the present invention is directed to a system for visualising a spatial surface curvature of a 3D-object. The system comprises a device for acquiring a dataset created by an imaging modality, wherein the dataset describes or characterises a 3D-shape the 3D-object. These means can be data processing device, for example, for accessing a data storage device or storage medium containing the dataset. Equally, these devices can comprise the imaging modality or a corresponding imaging device. The device for acquiring the dataset can, in other words, comprise for example an x-ray device, a magnetic resonance device (MR, MRI, MRT), a camera, and/or the like.

Another aspect of an embodiment of the present invention is directed to a system comprising:

a memory storing a dataset created via an imaging modality, the dataset describing a 3D-shape of a 3D-object; and at least one processor to acquire the dataset from the memory, adapt, in dependence on the 3D-shape of the 3D-object, a flat 2D-grid of intersecting grid lines to follow a surface curvature of the 3D-object to create an adapted grid, a distance between two neighbouring intersections, along the grid lines of the adapted grid following the surface curvature of the 3D-object, being equal to a respective corresponding distance between a respective two neighbouring intersections of the flat 2D-grid before the adapting, and output the adapted grid to a display for display of the adapted grid over at least one of the 3D-object and a virtual model of the 3D-object.

Another aspect of an embodiment of the present invention is directed to a system comprising:

an imaging modality to create a dataset, the dataset describing a 3D-shape of a 3D-object; and at least one processor to adapt, in dependence on the 3D-shape of the 3D-object, a flat 2D-grid of intersecting grid lines to follow a surface curvature of the 3D-object to create an adapted grid, a distance between two neighbouring intersections, along the grid lines of the adapted grid following the surface curvature of the 3D-object, being equal to a respective corresponding distance between a respective two neighbouring intersections of the flat 2D-grid before the adapting; and a display to display the adapted grid over at least one of the 3D-object and a virtual model of the 3D-object.

BRIEF DESCRIPTION OF THE DRAWINGS

Further advantages, features, and details of the present invention derive from the following description of preferred embodiments of the present invention as well as from the drawings pertaining to the present invention. The features and feature combinations previously mentioned in the description as well as the features and feature combinations mentioned in the following description of the figures and/or shown in the figures alone can be employed not only in the respectively indicated combination but also in other combinations or taken alone without leaving the scope of the present invention. In the drawings

Figure 1:
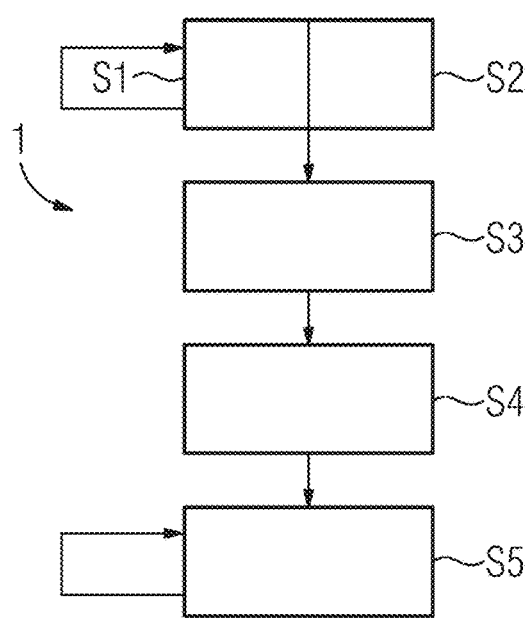
FIG. 1 shows an example embodiment of a schematic flow chart for a method for visualising a surface curvature of a 3D-object.

Matching or functionally equivalent features in the figures are indicated by the same reference signs.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method according to an embodiment of the present invention for visualising a spatial surface curvature of a 3D-object comprises multiple steps. In one step of the method a dataset created by way of an imaging modality is acquired, wherein the dataset describes or specifies a 3D-shape of the 3D-object. Imaging modalities in this sense can, for example, include or comprise radiography, magnetic resonance imaging, ultrasound or acoustic imaging, tomography, optical imaging using a camera, and the like. The 3D-shape of the 3D-object is or corresponds to the three-dimensional or volumetric form of the 3D-object. The surface of the 3D-object is in principle a 2D-object that is curved or bent in the third dimension. Parts or areas of the 3D-object or its surface that are strongly curved or, for example, extend in a relatively large angle from or with respect to a flat reference plane have a relatively higher surface curvature than flat areas or parts of the 3D-object or its surface.

Another step of the method according to an embodiment of the present invention comprises adapting a flat 2D-grid of intersecting grid lines in dependence on the 3D-shape of the 3D-object to follow or conform to the surface curvature of the 3D-object. This means that the flat 2D-grid is deformed according to the 3D-shape or the surface curvature of the 3D-object so that a distance between any two neighbouring intersections of grid lines along every or any grid line of the adapted or conformed grid following the surface curvature or 3D-shape of the 3D-object is equal to the respective corresponding distance between the respective two intersections of the non-adapted flat 2D-grid.

Another step of the method according to an embodiment of the present invention comprises applying the adapted or conformed grid, by overlaying for example, to the 3D-object and/or a virtual model of the 3D-object. Essentially the adapted grid is still a 2D-grid in the sense that at any point it can have substantially zero thickness. The adapted grid can, however, similarly considered to be a 2.5D- or 3D-object in the sense that it is bent or curved in the third dimension, just as the curved surface of the 3D-object itself.

Another way to understand the adaptation of the grid to the 3D-shape of the 3D-object is to first consider a flat 2D-grid with square grid cells in a flat 2D-plane that is not curved or bent in the third dimension. If seen perpendicular to the plane of the grid, the distance between two neighbouring intersections along any grid line is the same whether it is measured in the plane along the grid line or on a 2D-screen on which the flat 2D-grid is projected along the appendicular viewing direction.

This is, however, not always the case for the adapted grid. If the flat 2D-grid is adapted or conformed to the curved 3D-shape of the 3D-object in the described way so that the grid lines extend in or on the surface of the 3D-object, the distance between the two intersections is still the same when again measured along the grid line, i.e. when following the grid line on the surface of the 3D-object along its surface curvature.

If, however, the adapted grid is again projected on a 2D-screen and the distance between the two intersections is measured on this 2D-screen, then the distance can differ from the previous measurements. This is the case, because the grid lines of the adapted grid—at least to a certain degree—extend in or along the third dimension because of the 3D-curvature of the surface of the 3D-object. This is, however, not represented as a corresponding distance in the flat 2D-projection of the adapted grid onto the flat 2D-screen. By adapting the grid to follow the surface curvature of the 3D-object, the grid is, in other words, mapped onto the curved surface of the 3D-object.

By adapting the flat 2D-grid to the 3D-shape of the 3D-object, that is, by mapping the flat 2D-grid onto the 3D-object the adapted grid can effectively function as a more accurate ruler or measuring tape for distances along the curved surface of the 3D-object than a flat 2D-grid could. Thereby, at least one embodiment of the present invention can advantageously increase an accuracy and reliability of spatial mapping or correlation of objects with respect to the 3D-object and/or the 3D-object or parts thereof with respect to surrounding objects or reference points.

The adapted grid can for example indicate to a surgeon how far he has to move an instrument along the surface of the 3D-object to reach a certain point, or to traverse a certain area or region of interest on the surface of the 3D-object. This can advantageously allow for more accurate planning and execution of interventions and other procedures. Embodiments of the present invention can advantageously also help in visualising a model or virtual representation of the 3D-object, in particular when using a non-3D viewing device, such as a conventional electronic visual display. Embodiments of the present invention can therefore play an important role in improving usability and adaptation of modern 3D-visualisation techniques even for users that do not have access to or cannot use 3D-display technologies.

In an advantageous development of an embodiment of the present invention a segmentation or segmentation operation is performed on the dataset or a model or volume derived therefrom to indicate parts of the dataset, model, or volume belonging to the 3D-object. The segmentation does, in other words, define a volume making up the 3D-object to facilitate effective and precise processing or usability in further processing steps. The segmentation can be done automatically, semi-automatically, or manually.

The segmentation step takes into account that the dataset typically includes data or data points not belonging to or characterising the 3D-object. These data points therefore have to be distinguished from data or data points describing the 3D-object itself. This can advantageously allow for a more precise modelling of the 3D-object and a more precise overlaying of the 3D-object or its virtual model or representation with the adapted grid.

In another advantageous development of an embodiment of the present invention the adapted grid is added to or combined with the dataset and/or the virtual model of the 3D-object. This means that from the original dataset and the adapted grid an extended or augmented dataset is formed. The adapted grid can, for example, form or be treated as a texture that can be added to or overlaid on the surface of the 3D-object in the dataset or the virtual model or representation. This can advantageously simplify handling and further processing of the dataset, the virtual model, and the adapted grid for further processing steps and/or data storage. The extended or augmented dataset can then, for example, be exported to another application where it can be displayed with the adapted grid correctly overlaying the virtual model of the 3D-object without further processing or adaptation.

In another advantageous development of an embodiment of the present invention the 3D-object is a real physical object. A current pose, that is, a position and orientation, of the physical 3D-object is automatically tracked via a tracking system. The tracking system can, for example, use x-rays, ultrasound, a camera, a laser scanner, and/or an arrangement of electromagnets or coils or circuits for an image-based, optical, and/or electromagnetic tracking. The dataset is registered with the tracked current pose of the physical 3D-object. In other words, a coordinate system of the dataset and a coordinate system of the tracking system are registered or synchronised with each other to allow for easy and consistent combination of respective data and a correct representation of relative poses.

The adapted grid is then displayed corresponding to the tracked current pose of the physical 3D-object. This means, that the 3D-object and/or the virtual model can be correctly overlaid with the adapted grid in real-time. This in turn can advantageously allow for assessing and manipulating the 3D-object with improved precision and accuracy. Correctly displaying or overlaying the adapted grid in this sense means that a 3D-shape or curvature of the adapted grid is consistent with, that is, fits with or equals the shape or curvature of the 3D-object.

In a further advantageous development of an embodiment of the present invention, the adapted grid is displayed via an augmented reality device (AR-device) to appear on or in front of the current position of the physical object for a user or wearer of the augmented reality device. The augmented reality device preferably be or comprise a set of augmented reality glasses (AR-glasses) or a head-mounted display (HMD).

The adapted grid can, in other words, be displayed as a virtual structure or virtual object with its displayed position and orientation corresponding to, that is, depending on the tracked current pose of the physical 3D-object. This means, that without manipulating the physical 3D-object itself, the surface curvature and shape of the physical 3D-object can be visualised more clearly, consistently and reliably than simply relying on a perception of the 3D-object by the user. This can, for example, advantageously allow for consistently and precisely marking specific points of the physical 3D-object since the displayed adapted grid can serve as a ruler or measuring tape along the surface of the 3D-object.

In contrast to a physical ruler or measuring tape, however, the displayed adapted grid does advantageously not need to be handled manually or fixed to the physical 3D-object. It is a particular advantage of this method that the adapted grid can be displayed spatially correct relative to the physical 3D-object even if the physical 3D-object is not or not completely visible from a point of view of the user. The displayed adapted grid can then advantageously allow for accessing the physical 3D-object with improved precision. In particular, the user advantageously does not necessarily need to look away from the physical 3D-object to a separate screen or display for spatial references.

In a further advantageous development of an embodiment of the present invention, the adapted grid is projected onto the 3D-object or onto a surface covering the physical 3D-object via a laser projector and/or another light source in order to overlay the physical 3D-object with the adapted grid. The adapted grid is, in other words, shown on the physical 3D-object or the covering surface as a light pattern. This does advantageously neither hinder manipulation of the physical 3D-object in or use of any additional equipment or instruments by the user.

Another advantage of this method is that the projected adapted grid can consistently be seen by any personnel in a vicinity of the physical 3D-object without any need for synchronisation of respective views. The light pattern or laser beam can be adapted or diverted via one or more lenses and/or mirrors, for example, a digital micro-mirror device (DMD) to adapt the grid to the 3D-shape and surface curvature of the 3D-object as well as to any movement or motion of the physical 3D-object.

If, for example, the 3D-object is an internal structure of a patient, such as a bone, the covering surface might be a layer of tissue or a skin covering or surrounding the 3D-object, that is, the bone.

Regardless of whether the adapted grid is displayed via the augmented reality device, the laser projector, another light source, and/or any other device it can always indicate a position and the shape or surface curvature of the 3D-object to any viewer or user even if the covering surface or parts thereof are removed from between the user and the 3D-object or added between the user and the 3D-object.

It can be a particular advantage of this method that the displayed or projected adapted grid can be made up of grid lines or grid line segments, such as dashes, dots, and/or crosses and therefore does itself not obscure planar areas of the 3D-object and/or the covering surface.

In a further advantageous development of an embodiment of the present invention, a model of the 3D-object is displayed along with the adapted grid if the physical 3D-object is covered from a respective point of view of a respective user. The displayed model of the 3D-object can preferably be the virtual model already mentioned. It can preferably be displayed via the AR-device. It can, however, also be possible to display or project the model, at least in a simplified form, via a light source or the laser projector onto a covering surface or covering object that is covering or obscuring the real physical 3D-object.

Displaying the model and the adapted grid at or in front of the respective current position of the real physical 3D-object can advantageously illustrate a spatial relation between the 3D-object and surrounding objects or areas. This in turn can advantageously allow for accessing and/or manipulating the covered or obscured physical 3D-object with improved precision and reliability, as well as reduce distractions of a respective user since it is then not necessary for the user to look away from the location or direction of the physical 3D-object for example towards a separate display or monitor.

Along with displaying the model and the adapted grid, it can advantageously also be possible to display further anatomical structures in a vicinity of the physical 3D-object and/or information about the physical 3D-object and/or the addition of anatomical structures that may or may not also be covered, for example, through their location below one or more layers of skin or tissue.

Similar concepts as have been described in connection with the physical 3D-object can also apply to the case where the virtual model of the 3D-object is overlaid with the adapted grid. For example, the dataset may comprise data not only about the 3D-object itself but also about structures or objects in the vicinity of the 3D-object. The dataset may, for example, be comprise data about a whole section of a patient body with multiple different body parts and multiple different layers of different tissues. The adapted grid can then be displayed on an outer layer of skin or tissue that is covering the 3D-object which may for example be a bone. While the adapted grid is displayed on this covering layer skin or tissue, virtual markings or annotations can be made. The covering layer of skin or tissue can then be digitally faded out to reveal the virtual model of the 3D-object, while the adapted grid and the virtual markings and/or annotations can be kept displayed as a reference, for example for an instrument path or for planning an intervention or procedure.

In an advantageous development of an embodiment of the present invention, a user input adding any virtual markings and/or annotations to of the dataset, to the adapted grid, and/or to the virtual model of the 3D-object is automatically captured or tracked. The markings and/or annotations are then displayed along with the adapted grid. The adapted grid can, in other words, serve as a reference for the markings or annotations. The markings and/or annotations can for example indicate incision points, instrument paths, regions of interest, comments, instructions, and so on. By displaying the markings along with the adapted grid a spatial relation between the markings and the 3D-object can advantageously be illustrated at all times, in particular, even if the underlying physical 3D-object itself and/or the layer or covering surfer visible while the markings were made is not visible.

Displaying the markings also has the advantage that no physical markings on the physical 3D-object or a physical surface, tissue, or material covering the 3D-object are necessary. If, for example, the 3D-object is part of a patient, this can advantageously reduce a strain for the patient and/or reduce a risk of contamination or injury for the patient. While typically an outer layer of skin can be marked without any problems, these markings may get obscured during an intervention if they are covered with disinfection fluid or blood or if the skin is peeled back. Internal tissues typically cannot be marked as easily. In contrast, displaying the markings along with the adapted grid can advantageously be achieved independently of a current state of the patient or a stage of the respective procedure or intervention.

In an advantageous development of an embodiment of the present invention, a grid resolution defining a standard distance between two neighbouring grid lines is adjusted according to a corresponding user-given parameter value. The standard distance between two neighbouring grid lines can, for example, refer to or be defined as the distance between two parallel grid lines of the flat 2D-grid or of the adapted grid when it is adapted to a flat 2D-surface without any 3D-curvature. It is, in other words, then advantageously possible for a respective user to adjust the grid resolution manually as needed. For this purpose, a respective user input device or element or user input device can be provided. Adjusting the grid resolution can, for example, be done by entering a respective number as the corresponding parameter value or by adjusting a corresponding user input element such as a button or dial.

Making the grid resolution adjustable can advantageously allow for a flexible application of an embodiment of the present invention in different scenarios and use cases to adapt the grid resolution, that is, a cell size of cells of the adapted grid to a size and/or to the curvature of the 3D-object. Thereby, the visualisation of the surface curvature of the 3D-object can be optimised.

In a further advantageous development of an embodiment of the present invention, a region of interest of the 3D-object is indicated by displaying the grid lines in a part of the adapted grid covering the region of interest in a different colour than the grid lines outside of this part of the adapted grid. The region of interest can, in other words, be indicated or represented through a colour coding of the grid lines of the adapted grid. Since the adapted grid is displayed anyway this can advantageously reduce visual clutter and therefore improve visibility or perceptibility.

In an advantageous development of an embodiment of the present invention, a handle point or handler is displayed with the adapted grid. The handle point serves as a control element for a respective user to be able to shift, rotate, and/or pivot the displayed adapted grid. A user interaction with the handle point is automatically captured or tracked. The adapted grid is then shifted, rotated, and/or pivoted according to the tracked user interaction. The handle point can, in other words, function as a virtual user input element to allow the user to control and adjust a manner in which the adapted grid is displayed. This can provide the user with an improved flexibility allowing the present application to be advantageously used in a wide variety of use cases and applications.

The handle point can serve as a centre of rotation or as an anchor point for pivoting the adapted grid about it. It is, however, also possible to use a different point as the centre of rotation or as the anchor point for pivoting of the adapted grid. A respective centre of rotation and/or pivot point can also be displayed. Preferably, the centre of rotation and/or pivot point can be moved or shifted by the user manually which allows for further improved flexibility and adaptability of at least one embodiment of the present invention to different use cases and applications. It can, for example, be advantageous to rotate the adapted grid so that one or more of its grid lines align with a planned instrument path to allow for guiding the respective instrument with more ease and improved precision or accuracy.

Another aspect of an embodiment of the present invention is directed to a computer program product or computer program, comprising instructions that, when the computer program is executed by a computer, cause the computer to carry out a method according to an embodiment of the present invention for visualising a spatial surface curvature of a 3D-object.

The computer program product according to an embodiment of the present invention does, in other words, represent or encode the steps of the respective method or methods. The computer used for executing the computer program can in particular comprise a processor, a microchip, or a microcontroller, and a non-transitory computer-readable storage medium which is connected thereto and which contains the computer program or computer program product according to an embodiment of the present invention.

Such a non-transitory computer-readable storage medium having stored thereon a computer program product or computer program according to an embodiment of the present invention is in itself another embodiment of the present invention.

Correspondingly, another aspect of an embodiment of the present invention is directed to a data carrier signal carrying a computer program product or computer program according to an embodiment of the present invention.

Another aspect of an embodiment of the present invention is directed to a system for visualising a spatial surface curvature of a 3D-object. The system comprises a device for acquiring a dataset created by an imaging modality, wherein the dataset describes or characterises a 3D-shape the 3D-object. These means can be data processing device, for example, for accessing a data storage device or storage medium containing the dataset. Equally, these devices can comprise the imaging modality or a corresponding imaging device. The device for acquiring the dataset can, in other words, comprise for example an x-ray device, a magnetic resonance device (MR, MRI, MRT), a camera, and/or the like.

The system according to an embodiment of the present invention further comprises a device for adapting a flat 2D-grid of intersecting grid lines in dependence on the 3D-shape of the 3D-object to follow or conform to the surface curvature of the 3D-object so that a distance between any two neighbouring intersections along every grid line of the adapted or conformed grid following the surface curvature of the 3D-object is equal to the respective corresponding distance between the respective two intersections of the non-adapted flat 2D-grid. These devices can in particular comprise the computer referenced in connection with the computer program product according to an embodiment of the present invention.

The system according to an embodiment of the present invention further comprises a device for overlaying the 3D-object and/or a virtual model of the 3D-object with the adapted grid. These devices can also be or comprise the computer referenced in connection with the computer program product according to an embodiment of the present invention.

The system can also comprise a device for generating the virtual model or representation of the 3D-object from the dataset. The system can also comprise additional features and/or device(s), such as for example means for adjusting the grid resolution, the grid line colouring, a grid style, and so on. The system according to an embodiment of the present invention is, in other words, provided with means and adapted to carry out at least one embodiment of the method according to an embodiment of the present invention. For this purpose, the system may in particular comprise a computer-readable storage medium according to an embodiment of the present invention. Correspondingly, the system according to an embodiment of the present invention can have or comprise one or more of the features, properties characteristics, development, and/or parts or devices mentioned in connection with the other aspects and embodiments of the present invention, that is, the method, the computer program product, and the computer-readable storage medium.

The embodiments and developments of the present invention described herein for at least one aspect of the present invention, that is, for the method, the system, the computer program product, and the computer-readable storage medium, as well as the corresponding advantages may be applied to any and all aspects and embodiments of the present invention interchangeably.

The examples described below refer to preferred embodiments of the present invention. Therein, individual components and process steps of the embodiments each constitute individual, independent features of the present invention that can further develop the invention independently of each other as well as in combinations not explicitly described. The described embodiments can be further developed or supplemented by features, components and/or steps already described above.

FIG. 1 schematically shows an example of a flow chart 1 for an embodiment of a method for visualising a surface curvature of a 3D-object. For the present example it is assumed that the 3D-object is a part of a hip bone of a patient 20 (see FIG. 6). In a process step S1 of the method a position of the patient 20 and the bone is measured and continually tracked via a tracking system. The continuous tracking of the current pose of the patient 20 and the bone throughout the method is indicated by a looping arrow.

Parallel to tracking the pose of the patient 20 and the bone a dataset comprising raw x-ray- or magnetic resonance-data for the bone is acquired in a process step S2.

In a process step S3 the acquired dataset is used to reconstruct a 3D-image, volume, or model 2 (see FIG. 2) of the bone, that is, a virtual representation of the real physical bone. This comprises a segmentation operation, that is, segmenting the dataset or the reconstructed volume or image to indicate parts of the dataset and/or the reconstruction belonging to the bone as opposed to belonging to surrounding tissues.

Since the dataset is a 3D-dataset it and therefore the reconstructed volume, image, or model 2 of the 3D-object describes a 3D-shape of the 3D-object including its surface curvature.

In a process step S4 a grid of intersecting grid lines is projected onto the model 2 of the bone. To illustrate this FIG. 2 schematically shows at least a part of the model 2 of the hip bone.

Figure 2:
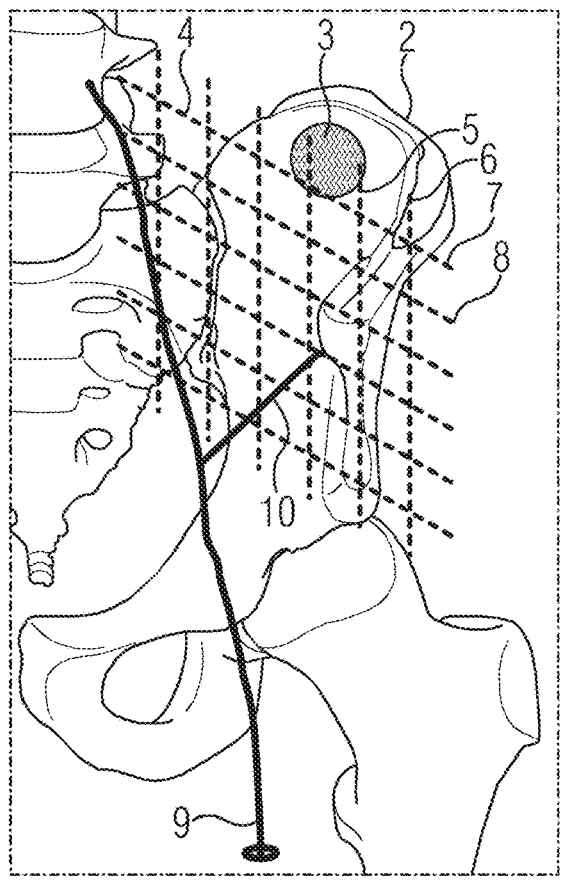
FIG. 2 schematically shows a 3D-object overlaid with a flat 2D-grid.

Radiological findings can comprise a rendering such as the model 2 overlaid with a flat grid 4 is shown in FIG. 2 to illustrate proportions, regions, and/or spatial relations on or regarding the real physical object or within a body of the patient 20. One such region can for example be a region of interest 3 indicated on the model 2. Grid lines of the flat grid 4 such as first and second lengthwise grid lines 5, 6, and first and second crosswise grid lines 7, 8 can then be used to better visualise a spatial relation or distance between the region of interest 3 and other parts of the model 2 and/or other parts of the body of the patient 20. Since the flat grid 4 is, however, only displayed as a flat plane in the virtual 3D-space in which the 3D-model 2 is displayed, an exact understanding of the spatial relations and distances can be difficult because the model 2 has an irregularly shaped curved surface.

Another way to illustrate this problem is trying to accurately determine a circumference of a 3D-object such as a tree trunk using only an inflexible ruler in a fixed spatial relation with the tree trunk, in particular when the tree trunk and the ruler are displayed or projected on a flat viewing screen.

An accurate understanding of the surface curvature of the bone and corresponding three-dimensional distances as well as distances along the surface of the bone can, for example, be crucial for optimal planning of a main instrument path 9 and/or a turnoff point on this main instrument path 9 for a turnoff path 10 to reach the region of interest 3 in a minimally invasive manner.

Looking at FIG. 2 a user might conclude that a diameter of the region of interest 3 along the surface of the model 2 or the corresponding real physical bone is larger than the distance between the first lengthwise grid line 5 and the second lengthwise grid line 6, and that the complete region of interest 3 is located above the first crosswise grid line 7. This is, however, an illusion caused by a perspective of the illustration and by a distance in a direction perpendicular to the plane of the flat grid 4 between the flat grid 4 and the region of interest 3 due to the surface curvature of the model 2 in three dimensions.

Figure 3:
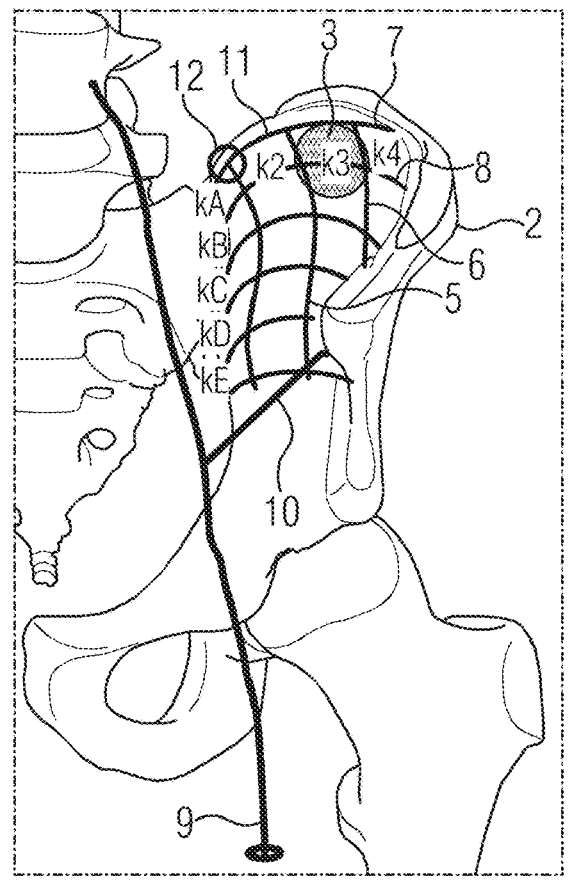
FIG. 3 schematically shows a 3D-object overlaid with an adapted grid.

Similarly to FIG. 2, FIG. 3 also schematically shows the model 2. Here the model 2 is, however, overlaid not with the flat grid 4 but with an adapted grid 11. The adapted grid 11 is adapted to the 3D-shape and the surface curvature of the model 2 so that the grid lines of the adapted grid 11 extend on the surface of the model 2 along and following its surface curvature. Because the adapted grid 11 is conforming to the surface curvature of the model 2 the respective distance between two grid lines of the adapted grid 11 accurately represents or corresponds to the distance on or along the surface of the model 2 and not along a straight line in empty space in front of the model 2.

On the basis of the adapted grid 11 it can clearly be seen that the diameter of the region of interest 3 is substantially equal to the distance between the first and second lengthwise grid lines 5, 6, and that the first crosswise grid line 7 actually marks an upper border instead of a lower border of the region of interest 3 with the region of interest 3 extending down from the first crosswise grid line 7 even across and below the second crosswise grid line 8.

With the help of the adapted grid 11 positions and distances on the model 2 and therefore on the corresponding real physical bone can thus be determined or assigned more accurately than on the basis of the flat grid 4.

Additionally, a virtual handle point or handle 12 is shown on the adapted grid 11 as well as a coordinate system or coordinate markings kA, kB, kC, kD, kE and k2, k3, k4 for the adapted grid 11. This coordinate system defines individual grid cells of the adapted grid 11 and thereby advantageously allows for unambiguous referencing of individual grid cells of the adapted grid 11 and correspondingly of specific parts of the model 2. In this example, the region of interest 3 substantially extends in the grid cells (kA,k3) and (kB,k3). The handle 12 serves as a virtual user interface and control element for shifting, rotating, and/or pivoting the adapted grid 11.

The methods described herein can advantageously be used for or in connection with radiological imaging for creating or annotating radiological findings as well as, for example, for interdisciplinary boards for discussion of individual patient cases. Also, the described methods and in particular the adapted grid 11 can be used as a reference for 3D-printing applications, for example, for preparation of a surgical intervention, as well as during an intervention through an augmented reality application which can allow for a more precise execution of the intervention. This could also be achieved or supported via a stereoscopic or 3D-camera, a laser, and/or the like. The laser or a laser projector 26 (see FIG. 6) can, for example, be used to directly project the adapted grid 11 and/or the region of interest 3, and/or additional markings or annotations to the physical body of the respective patient.

Figure 4:
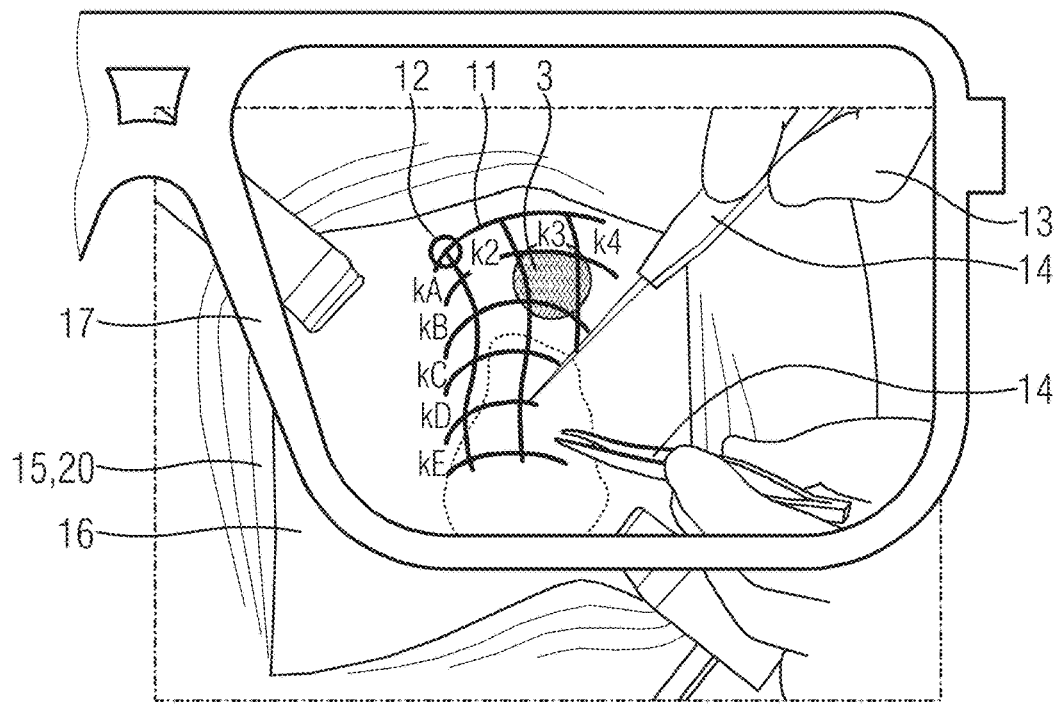
FIG. 4 schematically illustrates displaying an adapted grid as part of an augmented reality application.

FIG. 4 schematically illustrates an augmented reality application. Here, a user 13 uses an instrument 14 to manipulate a physical 3D-object, such as a patient 20. It might be a goal of the user 13 to access a bone that in the present example is still hidden by layers of skin 15 and tissue 16. The adapted grid 11 along with the handle 12 and the region of interest 3 is displayed overlaying an actual position of the bone via an augmented reality device which in this case is partially depicted as a set of AR-glasses 17.

Figure 5:
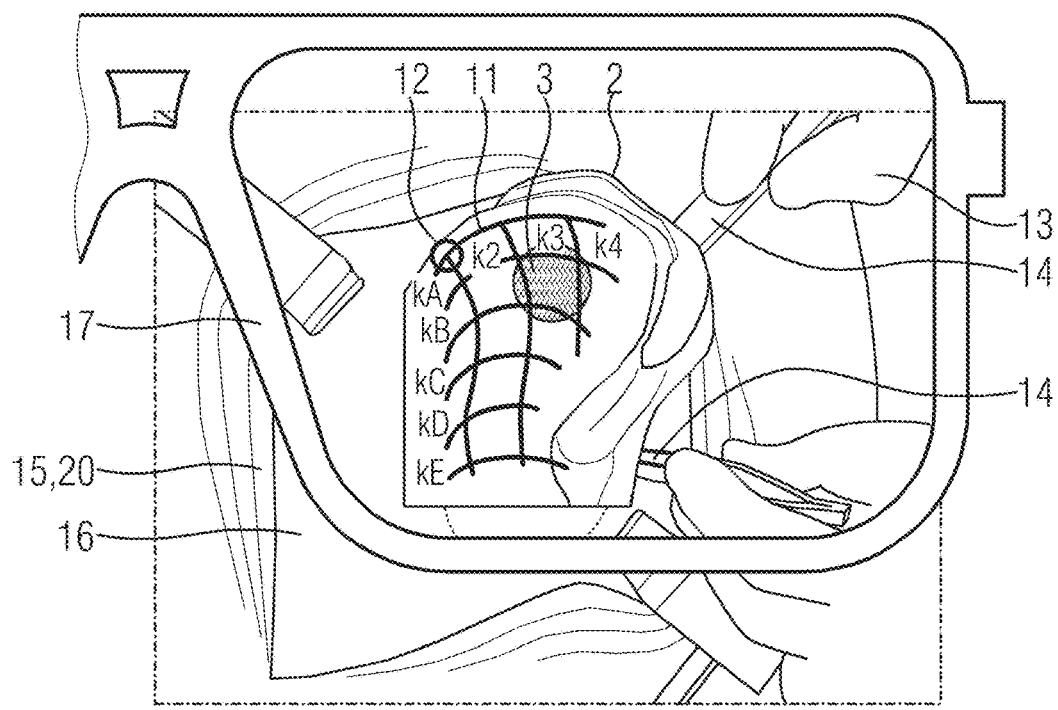
FIG. 5 schematically illustrates displaying an adapted grid and a virtual model of a 3D-object as part of an augmented reality application.

FIG. 5 schematically shows a further extension of the augmented reality application illustrated in FIG. 4. In FIG. 5 in addition to the adapted grid 11 at least a part of the model 2, that is, a virtual representation of the bone to be accessed is displayed using the AR-glasses 17. The model 2 as well as the adapted grid 11 are overlaid on top of or in front of the actual location of the physical bone on which the virtual model 2 is based. This can advantageously allow the user 13 to guide the instrument 14 towards the region of interest 3 even though the physical bone is still obscured by the tissue 16.

In a process step S5 a user interaction with the handle 12 is continually tracked or captured and the adapted grid 11 is adapted accordingly.

Figure 6:
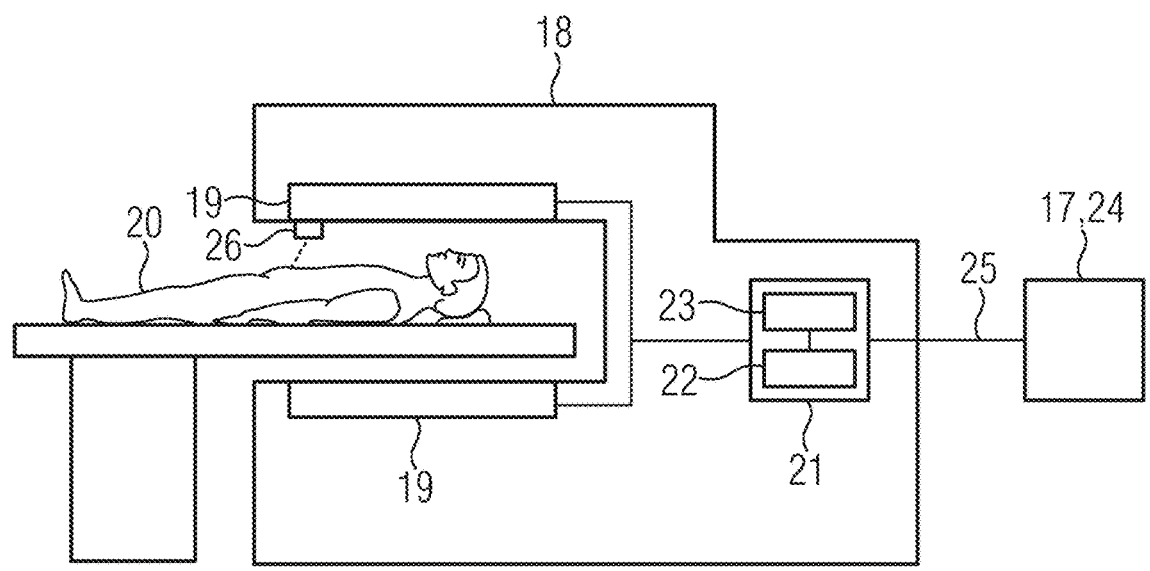
FIG. 6 shows a schematic illustration of an embodiment of a system for carrying out the method of FIG. 1.

FIG. 6 schematically shows an embodiment of a system 18 for performing the described method. The system 18 comprises a device 19 for acquiring the dataset—in this case for at least a part of the patient 20. The device 19 can for example comprise magnetic coils, and/or a radiation source and detector. The system 18 further comprises a data processing unit 21 connected to the means 19. The data processing unit 21 comprises a data storage medium 22 on which a computer program, that is, a program code is stored. The data processing unit 21 further comprises a microprocessor 23 connected to the data storage medium 22. The microprocessor 23 is adapted to execute the computer program or program code stored on the data storage medium 22 to execute the described process steps S1 to S5. The data processing unit 21 is further configured to output the adapted grid 11 to a display device 24. The display device 24 can be or comprise the set of AR-glasses 17 and/or a display or monitor or the like. A data connection 25 between the data processing unit 21 and the display device 24 can be wired or wireless. Presently, the system 18 further comprises a laser projector 26 for projecting the adapted grid 11 onto the patient 20.

Overall, the described examples show how extending a flat 2D-grid to have a curvature in a third dimension corresponding to a respective three-dimensional object of interest can facilitate an improved perceptibility of a spatial situation for example to improve a spatial correlation or mapping of specific points on the three-dimensional object.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing a surface curvature of a 3D-object, the method comprising:
acquiring a dataset generated via an imaging modality, the dataset describing a 3D-shape of the 3D-object;
reconstructing a virtual representation of the 3D-object from the dataset;
displaying a flat 2D-grid of intersecting grid lines over the virtual representation of the 3D-object;
generating an adapted grid of intersecting grid lines by adapting the flat 2D-grid to follow a surface curvature of the virtual representation of the 3D-object, wherein a distance along a grid line between two neighboring intersections on the adapted grid is equal to a distance along a grid line between two neighboring sections of the flat 2D-grid, and the two neighboring intersections on the adapted grid correspond to the two neighboring intersections on the flat 2D-grid; and outputting the adapted grid for display over at least one of the 3D-object or a virtual model of the 3D-object.

2. The method of claim 1, further comprising:

segmenting the dataset, wherein the segmenting of the dataset defines a volume of the dataset belonging to the 3D-object.

3. The method of claim 1, further comprising:

adding the adapted grid to at least one of the dataset or the virtual model of the 3D-object.

4. The method of claim 1, wherein the 3D-object is a physical 3D-object, and the method further comprises:

automatically tracking, via a tracking system, a current position and a current orientation of the physical 3D-object, registering the dataset with the current position and the current orientation of the physical 3D-object, and displaying the adapted grid corresponding to the current position and the current orientation of the physical 3D-object.

5. The method of claim 4, further comprising:

displaying, via an augmented reality device, the adapted grid to appear on or in front of the current position of the physical 3D-object, from a perspective of the augmented reality device.

6. The method of claim 4, further comprising:

projecting the adapted grid via a laser projector onto the physical 3D-object or onto a surface between the physical 3D-object and the laser projector.

7. The method of claim 4, further comprising:

displaying a model of the physical 3D-object along with the adapted grid via a display device, wherein a surface is between the physical 3D-object and the display device.

8. The method of claim 1, further comprising:

adding virtual markings to at least one of the dataset, the adapted grid, or the virtual model of the 3D-object;

automatically capturing the virtual markings; and outputting the virtual markings for display along with the adapted grid.

9. The method of claim 1, further comprising:

adjusting a grid resolution defining a standard distance between two neighboring grid lines according to a corresponding parameter value.

10. The method of claim 1, further comprising:

displaying intersecting grid lines of the adapted grid covering a region of interest in a first color; and displaying intersecting grid lines of the adapted grid not covering the region of interest in at least one second color, the first color and the at least one second color being different.

11. The method of claim 1, further comprising:

displaying the adapted grid and displaying a handle point with the adapted grid, the handle point serving as a control element for at least one of shifting, rotating, or pivoting the adapted grid;

tracking the handle point; and at least one of shifting, rotating, or pivoting the adapted grid according to the tracking.

12. A non-transitory computer program product, storing program code including instructions that, when the program code is executed by a computer, cause the computer to carry out the method of claim 1.

13. A non-transitory computer-readable storage medium storing a computer program including instructions that, when executed by a computer, cause the computer to carry out the method of claim 1.

14. A system for visualizing a surface curvature of a 3D-object, the system comprising:

a means for acquiring a dataset generated via an imaging modality, the dataset describing a 3D-shape of the 3D-object;

a means for reconstructing a virtual representation of the 3D-object from the dataset;

a means for displaying a flat 2D-grid of intersecting grid lines over the virtual representation of the 3D-object;

a means for generating an adapted grid of intersecting grid lines by adapting the flat 2D-grid to follow a surface curvature of the virtual representation of the 3D-object, wherein a distance along a grid line between two neighboring intersections on the adapted grid is equal to a distance along a grid line between two neighboring intersections of the flat 2D-grid, and the two neighboring intersections on the adapted grid correspond to the two neighboring intersections on the flat 2D-grid; and a means for outputting the adapted grid for display over at least one of the 3D-object or a virtual model of the 3D-object.

15. The method of claim 1, wherein the 3D-object is a physical 3D-object, and the method further comprises:

displaying, via an augmented reality device, the adapted grid to appear on or in front of a current position of the physical 3D-object, from a perspective of the augmented reality device.

16. The method of claim 1, wherein the 3D-object is a physical 3D-object, and the method further comprises:

projecting the adapted grid via a laser projector onto the physical 3D-object or onto a surface between the physical 3D-object and the laser projector.

17. The method of claim 1, wherein the 3D-object is a physical 3D-object, a surface is between the physical 3D-object and a display device, and the method further comprises:

displaying a model of the 3D-object along with the adapted grid via the display device.

18. A system, comprising:

a memory storing a dataset generated via an imaging modality, the dataset describing a 3D-shape of a 3D-object; and at least one processor configured to reconstruct a virtual representation of the 3D-object from the dataset, display, via a display, a flat 2D-grid of intersecting grid lines over the virtual representation of the 3D-object, generate an adapted grid of intersecting grid lines by adapting the flat 2D-grid to follow a surface curvature of the 3D-object, wherein a distance along a grid line between two neighboring intersections on the adapted grid is equal to a distance along a grid line between two neighboring intersections of the flat 2D-grid, and the two neighboring intersections on the adapted grid correspond to the two neighboring intersections on the flat 2D-grid, and output the adapted grid for display over at least one of the 3D-object or a virtual model of the 3D-object.

19. A system comprising:

an imaging modality to generate a dataset, the dataset describing a 3D-shape of a 3D-object; and at least one processor configured to
reconstruct a virtual representation of the 3D-object from the dataset,
display, via a display, a flat 2D-grid of intersecting grid lines over the virtual representation of the 3D-object,
generate an adapted grid of intersecting grid lines by adapting the flat 2D-grid to follow a surface curvature of the virtual representation of the 3D-object, wherein
a distance along a grid line between two neighboring intersections on the adapted grid is equal to a distance along a grid line between two neighboring sections of the flat 2D-grid, and
the two neighboring intersections on the adapted grid correspond to the two neighboring intersections on the flat 2D-grid; and
display, via the display, the adapted grid over at least one of the 3D-object or a virtual model of the 3D-object.

20. The system of claim 19, wherein the display includes at least one of AR-glasses or a display monitor.

* * * * *